(12) United States Patent
Sangi et al.

(10) Patent No.: US 9,120,661 B2
(45) Date of Patent: *Sep. 1, 2015

(54) PROCEDURE AND APPARATUS FOR THE TREATING CONTAINERS SUCH AS PLASTIC BOTTLES IN A BOTTLE FILLING PLANT OR CONTAINERS IN A CONTAINER FILLING PLANT

(75) Inventors: Daryoush Sangi, Hamburg (DE); Thomas Herold, Ahrensburg (DE)

(73) Assignee: KHS GmbH, Dortmund (DE)

( * ) Notice: Subject to any disclaimer, the term of this patent is extended or adjusted under 35 U.S.C. 154(b) by 1093 days.

This patent is subject to a terminal disclaimer.

(21) Appl. No.: 12/605,576

(22) Filed: Oct. 26, 2009

(65) Prior Publication Data

US 2010/0276029 A1 Nov. 4, 2010

Related U.S. Application Data

(63) Continuation-in-part of application No. PCT/EP2008/002858, filed on Apr. 11, 2008, and a continuation-in-part of application No. PCT/EP2008/003247, filed on Apr. 23, 2008.

(30) Foreign Application Priority Data

Apr. 27, 2007 (DE) .......... 10 2007 020 457
Apr. 27, 2007 (DE) .......... 10 2007 020 458

(51) Int. Cl.
  *B65B 55/10* (2006.01)
  *A61L 2/20* (2006.01)
  (Continued)

(52) U.S. Cl.
  CPC .......... *B67C 7/0073* (2013.01); *A61L 2/18* (2013.01); *A61L 2/208* (2013.01); *B08B 9/26* (2013.01); *B65B 55/10* (2013.01)

(58) Field of Classification Search
  CPC .............. B65B 55/10; A61L 2/208

USPC ........ 423/272, 273; 422/28, 29, 30, 292, 302, 422/105, 108, 110; 53/253, 331.5, 317, 53/319, 426

See application file for complete search history.

(56) References Cited

U.S. PATENT DOCUMENTS

| 2,123,145 A | 7/1938 | Peiler |
| 2,974,446 A | 3/1961 | Poting |

(Continued)

FOREIGN PATENT DOCUMENTS

| DE | 198 46 322 A1 | 4/2000 |
| DE | 199 49 692 A1 | 4/2001 |

(Continued)

OTHER PUBLICATIONS

International Search Report PCT/EP2008/002858 and English translation thereof.

(Continued)

*Primary Examiner* — Stephen F Gerrity
*Assistant Examiner* — Joy N Sanders
(74) *Attorney, Agent, or Firm* — Nils H. Ljungman & Associates (57) ABSTRACT

Method and apparatus for sterilizing containers with a sterilization medium. The method involves first introducing a sterilization medium into a container, and then introducing a heated gaseous and/or vaporous activation medium into the container. The activation medium is used to heat and activate the sterilization medium to destroy microorganisms. At least one parameter of the method is controlled based on the detected temperature of the container or the wall of the container. Alternatively, the heating and activating of the sterilization medium is achieved by first introducing an activation medium into the container under time control at a constant temperature and at a first, constant, volume flow, and then subsequently adjusting to a second, different, volume flow.

16 Claims, 3 Drawing Sheets

(51) Int. Cl.
  *B67C 7/00*  (2006.01)
  *A61L 2/18*  (2006.01)
  *B08B 9/26*  (2006.01)

(56) References Cited

U.S. PATENT DOCUMENTS

| | | | |
|---|---|---|---|
| 4,354,095 A * | 10/1982 | de Vries | 219/388 |
| 5,398,734 A | 3/1995 | Hartel | |
| 6,702,985 B1 | 3/2004 | Taggart et al. | |
| 6,875,399 B2 * | 4/2005 | McVey | 422/3 |
| 2002/0029543 A1 * | 3/2002 | Taggart | 53/426 |
| 2004/0191112 A1 * | 9/2004 | Hill et al. | 422/3 |
| 2006/0032189 A1 | 2/2006 | Giacobbe | |
| 2009/0130268 A1 | 5/2009 | Euler et al. | |

FOREIGN PATENT DOCUMENTS

| | | |
|---|---|---|
| DE | 10 2004 030 956 | 1/2006 |
| DE | 10 2004 030957 | 1/2006 |
| DE | 10 2005 018 382 | 10/2006 |
| EP | 0 590 505 A1 | 4/1994 |
| JP | 2003512260 | 4/2003 |
| JP | 2006509690 | 3/2006 |
| WO | WO 2006/053745 A1 | 5/2006 |
| WO | WO 2007/134803 A | 11/2007 |

OTHER PUBLICATIONS

German Search Report 10 2007 020 458.4.

* cited by examiner

PROCEDURE AND APPARATUS FOR THE TREATING CONTAINERS SUCH AS PLASTIC BOTTLES IN A BOTTLE FILLING PLANT OR CONTAINERS IN A CONTAINER FILLING PLANT

CONTINUING APPLICATION DATA

This application is a Continuation-In-Part application of International Patent Application No. PCT/EP2008/002858, filed on Apr. 11, 2008, which claims priority from Federal Republic of Germany Patent Application No. 10 2007 020 458.4, filed on Apr. 27, 2007. International Patent Application No. PCT/EP2008/002858 was pending as of the filing date of this application. The United States was an elected state in International Patent Application No. PCT/EP2008/002858.

This application is also a Continuation-In-Part application of International Patent Application No. PCT/EP2008/003247, filed on Apr. 23, 2008, which claims priority from Federal Republic of Germany Patent Application No. 10 2007 020 457.6, filed on Apr. 27, 2007. International Patent Application No. PCT/EP2008/003247 was pending as of the filing date of this application. The United States was an elected state in International Patent Application No. PCT/EP2008/003247.

BACKGROUND

1. Technical Field

The present application relates to a procedure and apparatus for the treating containers such as plastic bottles in a bottle filling plant or containers in a container filling plant.

2. Background Information

Background information is for informational purposes only and does not necessarily admit that subsequently mentioned information and publications are prior art.

A beverage bottling plant for filling bottles with a liquid beverage filling material can possibly comprise a beverage filling machine, which is often a rotary filling machine, with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material.

Some beverage bottling plants may possibly comprise filling arrangements that receive a liquid beverage material from a toroidal or annular vessel, in which a supply of liquid beverage material is stored under pressure by a gas. The toroidal vessel may also be connected to at least one external reservoir or supply of liquid beverage material by a conduit or supply line. In some circumstances it may even be possible that a beverage bottling plant has two external supply reservoirs, each of which may be configured to store either the same liquid beverage product or different products. These reservoirs could possibly be connected to the toroidal or annular vessel by corresponding supply lines, conduits, or other arrangements. It is also possible that the external supply reservoirs could be in the form of simple storage tanks, or in the form of liquid beverage product mixers.

A wide variety of types of filling elements are used in filling machines in beverage bottling or container filling plants for dispensing a liquid product into bottles, cans or similar containers, including but not limited to filling processes that are carried out under counterpressure for the bottling of carbonated beverages. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine.

After a filling process has been completed, the filled beverage bottles are transported or conveyed to a closing machine, which is often a rotary closing machine. A revolving or rotary machine comprises a rotor, which revolves around a central, vertical machine axis. There may further be provided a conveyer arrangement configured to transfer filled bottles from the filling machine to the closing station. A transporting or conveying arrangement can utilize transport star wheels as well as linear conveyors. A closing machine closes bottles by applying a closure, such as a screw-top cap or a bottle cork, to a corresponding bottle mouth. Closed bottles are then usually conveyed to an information adding arrangement, wherein information, such as a product name or a manufacturer's information or logo, is applied to a bottle. A closing station and information adding arrangement may be connected by a corresponding conveyer arrangement. Bottles are then sorted and packaged for shipment out of the plant.

Many beverage bottling plants may also possibly comprise a rinsing arrangement or rinsing station to which new, non-return and/or even return bottles are fed, prior to being filled, by a conveyer arrangement, which can be a linear conveyor or a combination of a linear conveyor and a starwheel. Downstream of the rinsing arrangement or rinsing station, in the direction of travel, rinsed bottles are then transported to the beverage filling machine by a second conveyer arrangement that is formed, for example, by one or more starwheels that introduce bottles into the beverage filling machine.

It is a further possibility that a beverage bottling plant for filling bottles with a liquid beverage filling material can be controlled by a central control arrangement, which could be, for example, a computerized control system that monitors and controls the operation of the various stations and mechanisms of the beverage bottling plant.

The sterilization of packaging containers of the type used in the food and beverage industry, for example, is becoming increasingly important because a long shelf life of the contents of the container without the addition of preservatives or a subsequent treatment, e.g. by pasteurization, is becoming increasingly unattractive on account of its negative effect on the packaged product.

To prevent, restrict, and/or minimize this, for example, aseptic filling machines are used to fill bottles. For this purpose, the entire bottling plant or a portion of the bottling plant may be operated in a sterile environment. To achieve this sterile environment, the plant may be enclosed in a housing, the interior is sterilized and kept as sterile as possible, and steps are taken to essentially ensure or promote that the air and all or most other substances that are introduced into the interior are practically sterile. An essential component of this process is also that the interior of the containers to be filled are also sterilized.

Containers, for example beverage bottles, cans, medicament or medicine bottles, or medicament or medicine cans, must or should often be sterilized prior to filling so as to prevent, restrict, and/or minimize the material to be filled from spoiling or going bad. In the cooperation with the aseptic treatment installations or aseptic treatment stations and the filling installations or filling stations, filling of the containers can occur thus under clean room or clean space conditions by means of which a subsequent sterilization, e.g. by heating of the container together with the container contents, can be avoided, restricted, and/or minimized, which is desirable under certain circumstances as pertains to the quality and/or the taste of the filling material or the bottled material.

Some methods for sterilizing bottles, cans or similar containers use a sterilization medium that comprises hydrogen peroxide, i.e. use a sterilization medium (below also hydrogen peroxide sterilization medium) that comprises hydrogen peroxide mixed with hot sterile air. In the case of these methods, which are used, for example, for sterilizing containers for beverages, but also for sterilizing containers or packages for other products, such as, for example, medicines, a hydrogen peroxide condensation film is formed on the inside surface of the cooler container through condensation when introducing the hot hydrogen peroxide sterilization medium, said condensation film being activated in a subsequent activating phase, by introducing a sterile hot gaseous and/or vaporous activating medium, for example, by introducing hot sterile air, in such a manner that through the decomposition of hydrogen peroxide, free oxygen radicals are created that react with existing germs and contaminants for the sterilization of the containers.

In these methods the sterile air used as activation medium is heated to the activation temperature by conducting it through a heat exchanger heated to a temperature between one hundred thirty degrees Celsius and one hundred fifty degrees Celsius. Then, in a step following the activation phase, the containers are blown upon and cooled down with the sterile air, which is supplied to the container at a temperature distinctly below the activation temperature. For this, the sterile air is taken at a correspondingly high volume flow through the heat exchanger, preventing it from becoming heated to the activation temperature.

Furthermore, some methods and devices for the treatment of bottles or such containers use a hot treatment medium which is introduced into the containers. Thanks to temperature sensors, the temperature of the containers is detected before and after the heat treatment, or the temperature of the treatment medium flowing back out, and the temperature of the hot treatment medium and/or the intensity of the treatment is controlled as a function of the measured temperatures. No treatment with a treatment medium comprising hydrogen peroxide is provided.

OBJECT OR OBJECTS

It is an object of the present application to provide a method and a device with which, while maintaining a high rate of sterilization, i.e. a high quality of sterilization, it is possible to reduce the duration of the treatment overall, and at the same time in one possible embodiment also to reduce the duration of the activating phase, with the treatment of the containers being gentle.

SUMMARY

This object is achieved through a method for sterilizing bottles, cans or similar containers by introducing vaporous hydrogen peroxide or a hot hydrogen peroxide sterilization medium into the respective container in an application phase and by activating the hydrogen peroxide sterilization medium in an activating phase by introducing a sterile gaseous and/or vaporous hot activating medium, in one possible embodiment by introducing hot sterile air into the respective container. At least during a part phase of the activating phase, the volume flow of the activating medium introduced into the respective container is controlled in dependence on the container temperature or on the temperature of the wall of the container. The device is realized as a sterilizing device for containers, such as bottles, beakers, cans and the like for accomplishing the method according to the present application. The sterilization device has at least one device for measuring the temperature of solid body surfaces in a contactless manner and, connected thereto, a computer-controlled control and regulating device for evaluating the measured values and for regulating the temperature and/or volume flow.

With the method and the device according to the present application, there is a considerable reduction in the duration of the method and at the same time in one possible embodiment a reduction in the overall duration of the activating phase. At the same time, the treatment is also gentle and avoids, restricts, and/or minimizes overloading the containers in a thermal manner whilst providing high quality sterilization or high rates of sterilization. The method according to the present application is consequently suitable in one possible embodiment for containers produced from plastics material, e.g. from PET.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

Further developments of the present application are an object of the present application. The present application is explained below in conjunction with the Figures of a possible embodiment, in which, in detail.

DESCRIPTION OF EMBODIMENT OR EMBODIMENTS

Disclosed herein is a method for sterilizing bottles, cans or similar containers by introducing vaporous hydrogen peroxide or a hot hydrogen peroxide sterilization medium into the respective container in an application phase and by activating the hydrogen peroxide sterilization medium in an activating phase by introducing a sterile gaseous and/or vaporous hot activating medium, in one possible embodiment by introducing hot sterile air into the respective container.

Figure 1:
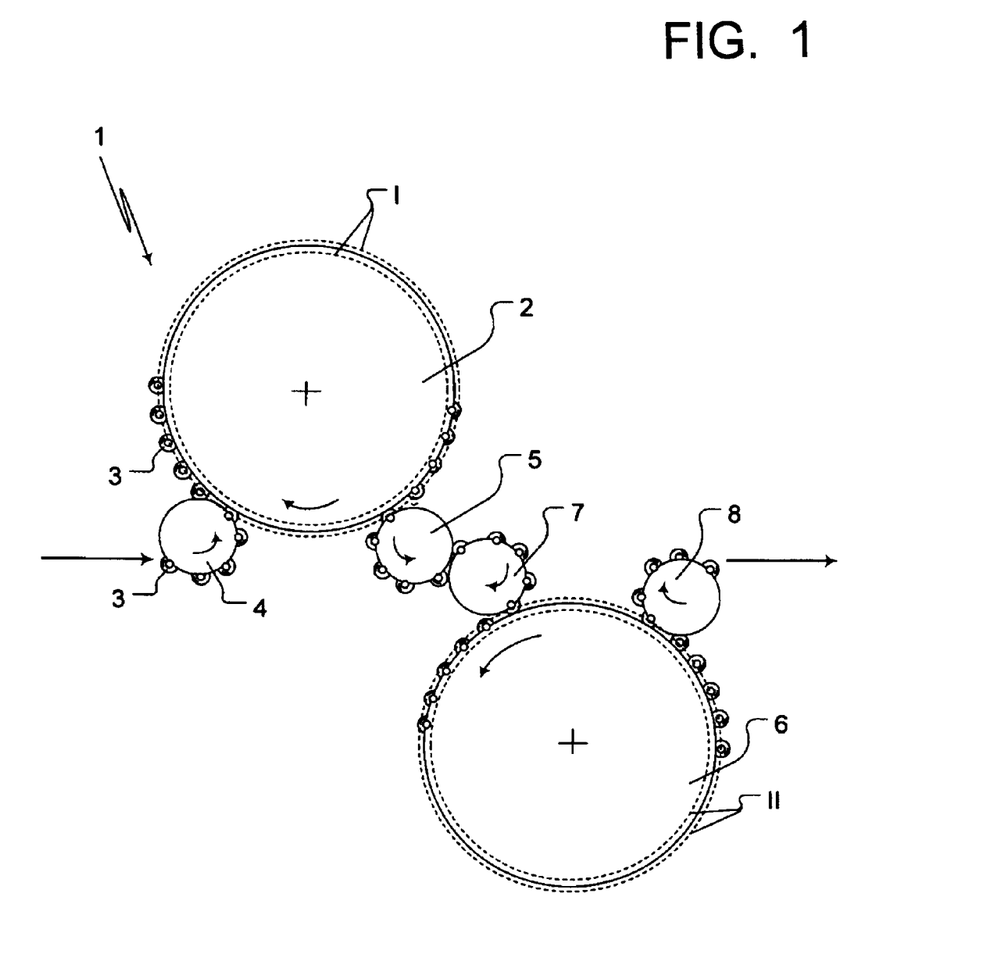
FIG. 1 shows a very simplified representation and top view of a machine or device for accomplishing the method according to the present application.

The device for sterilizing bottles, identified in general in the Figure by the reference 1, or respectively the method show a rotor 2, which is rotatingly driveable about a vertical machine axis for the application of the sterilizing means into the bottles 3 to be treated, which are supplied via a container inlet star 4, and from which the treated bottles 3, i.e. the moistened bottles 3 are removed via a container outlet 5 and supplied to the subsequent activator. The activator is also a rotor 6 that is rotatingly driveable about a vertical machine axis for activating the sterilizing means by means of sterile hot air, which is conducted into the bottles 3 to be treated. The bottles 3 are supplied to the rotor 6 via a container inlet star 7 and the treated, i.e. sterilized bottles 3 are removed via a container outlet 8 and are supplied to the subsequent method step, in one possible embodiment, a filler.

Application heads are provided in a known manner on the rotor 2 above each bottle opening, said application heads rotating with the rotor 2 and being indicated as double broken lines 1. A bottle or container carrier 14 is associated with each application head on the rotor 2, on which bottle or container carrier the respective bottle 3 is retained below the treatment head 6 during the treatment, in the case of the possible embodiment, a bottle 3 realized as a PET bottle, is suspended at the side of the bottle at a mouth flange.

The moistening of the surfaces of the bottles 3 is effected by using the hydrogen peroxide sterilization medium, which is heated in a known manner inside the respective treatment head to a temperature $T_1$ of, for example, one hundred forty-five degrees Celsius by spraying in hydrogen peroxide, for example thirty-five percent hydrogen peroxide into sterile air and by heating the aerosol obtained in this manner.

For the treatment, hot hydrogen peroxide sterilization medium is introduced into the interior of the bottle 3 in such a manner that, through condensation on the inside surface of the bottle 3, which is colder compared to the temperature $T_1$ of the hydrogen peroxide sterilization medium, an hydrogen peroxide condensation film is formed uniformly covering at least the entire inside surface of the respective bottle 3 with an hydrogen peroxide condensation film.

Following said application phase and after the bottles, moistened in this manner, have been conducted to the rotor 6, the hydrogen peroxide condensation film is activated in another treatment phase, i.e. in an activating phase. To this end, analogous to the design and arrangement at the rotor 2, activator heads 9 (FIG. 2) are positioned in a known manner above each bottle opening, said activator heads rotating with the rotor 6 and being indicated simply as double broken lines II in FIG. 1. The activating is started through the application of energy, by introducing a hot sterile gaseous and/or vaporous medium, for example by introducing hot sterile air at a temperature $T_2$ into the respective bottle 3 through a tube 10 (FIG. 2) that is inserted into said bottle. This activating process results in a decomposition reaction of hydrogen peroxide, in the course of which, among other things, free oxygen radicals are created which react with existing germs and/or contaminants in the respective bottle 3 and thus effect sterilization of the same. The hot sterile air used in the activating phase at the same time also causes the respective bottle to dry. Sterilization methods with said method steps are known in principle.

The method according to the present application stands out compared to known methods by a special development of the individual treatment phases or respectively of their method steps.

In the application phase, the hot hydrogen peroxide sterilization medium is introduced at a constant or substantially constant temperature $T_1$ and for a constant or substantially constant discharge or application time, for example for a discharge time of 3 seconds for bottles or containers with a volume of five hundred milliliters. The volume flow $v_1$ of the hot hydrogen peroxide sterilization medium introduced into the respective bottle 3, in this case, is also constant or substantially constant, for example, during the application time.

Figure 2:
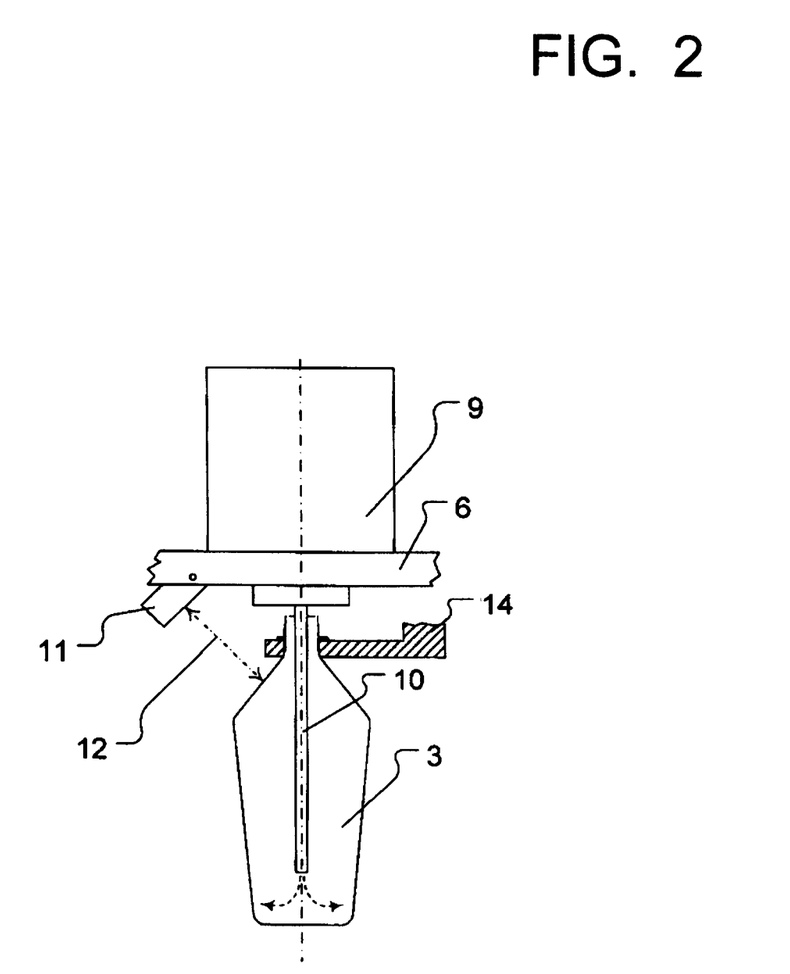
FIG. 2 shows a very simplified representation of a treatment head of the device in FIG. 1.

The activating of the hydrogen peroxide condensation film in the respective bottle 3 is effected during the activating phase in two method steps or activating steps. During a first method step, the hot sterile air used for the activating process is introduced into the bottle 3 via the tube 10 at a temperature $T_2$ and at a constant or substantially constant, large volume flow $v_2$. This introducing is carried out, for example, for a predetermined discharge time of x seconds or until the temperature of the container wall $T_{BW}$ of the respective bottle 3 has reached a predetermined required and/or desired temperature $T_{BWrequired}$ that is monitored and/or controlled by a pyrometer 11 (FIG. 2). The dot dash arrow 12 indicates the measuring procedure. The overall duration of this first method step is around four to five seconds.

In a subsequent further method step, the hot activating medium, which, in its turn, is in one possible embodiment hot sterile air, is then introduced into the bottle 3 at the temperature $T_3$ and at a volume flow $v_3$ for a discharge duration of y seconds. The volume flow $v_3$, which is less than the volume flow $v_2$, in this case is controlled in dependence on the container temperature $T_{BW}$ of the respective bottle 3 in such a manner that also during this second method step of the activating phase, the container temperature $T_{BW}$ has the required and/or desired temperature $T_{BWrequired}$. $T_3$ is identical to $T_2$ and the volume flow $v_3$ is adjusted via a throttle in the line path of the sterile air.

The required and/or desired temperature $T_{BWrequired}$, in this case, in the two method steps is below a temperature that would lead to an excessive load or deforming or to damage of the bottles 3. As the temperature of the bottle wall is monitored, a steep heating gradient can be selected and the temperature in the second activating step can be kept very high. This has not been possible in known systems for safety reasons (deformation of the bottle).

The following volume flows are produced in the activating phase in a test stand for bottles with a bottle volume of five hundred milliliters:

$v_2$=9.7 Nm$^3$/h $v_3$=4.2 Nm$^3$/h

The container temperature $T_{BW}$ is also measured in the second method step in a contactless manner by using at least one pyrometer 11, as is indicated in FIG. 2. Depending on the structure of the rotor 6 and on the activator head associated therewith and on the container material, other contactless heat measuring systems can also be used. In the case of the variant shown in FIG. 2, the pyrometer 11 is mounted so as to be rotatable in order to be able to be aligned in an optimum manner depending on the bottle or container geometry.

In one possible embodiment of the method according to the present application, the activating process is much stronger, consequently making it possible to shorten the duration of the treatment in a considerable manner, i.e. making it shorter than ten seconds. In one possible embodiment of the present application in the high performance range, i.e. in the case of a high output system that includes the device 1 (number of bottles 3 processed per unit time) where up to now it has been necessary and/or desired to connect an additional second activator downstream of the rotor 6, the activating phase can now be carried out purely on the rotor 6 or the rotor 6 can have a clearly smaller diameter if two activator rotors are to be provided. This also means that even with reduced expenditure on the machine, a considerable increase in machine performance is possible. In one possible embodiment, it is possible to carry out the application phase and the activating phase on one single rotor.

As the method according to the present application is based on automatic control of at least the volume flow $v_3$ in the second method step of the activating phase, it is no longer necessary or may not be desired for the operator of a system to carry out time-consuming adjustments or trials to achieve optimum sterilization of bottles or similar containers. The respective system, rathermore by way of manufacturer specifications that take into account the different container forms and/or materials, can be easily adjusted and operated, the activating phase or the method steps therein being carried out or controlled automatically by the control unit that is internal to the system.

The essential parameters of an embodiment of the method according to the present application for sterilizing bottles 3 with a volume of five hundred milliliters can be summarized as follows:

Application Phase

| | |
|---|---|
| Hydrogen peroxide concentration in the hydrogen peroxide sterilization medium: | 20% |
| Maximum container temperature $T_{BW}$: | around 35° C.-42° C. |
| Temperature $T_1$: | around 145° C. |
| Pressure of the hydrogen peroxide sterilization medium: | around 0.7 bars |
| Volume flow $v_1$: | around 1.5 l/bottle |
| Volume flow $v_1$: | around 2.7 Nm³/h |

Activating Phase—Method Step 1

| | |
|---|---|
| Maximum container temperature $T_{BW}$: | around 67° C.-68° C. |
| Volume flow $v_2$: | around 10.8 l/bottle 9.7 Nm³/h |
| Vapor pressure: | around 1.0 bar |
| Air pressure: | around 1.5 bars |

Activating Phase—Method Step 2

| | |
|---|---|
| Container temperature $T_{BW}$: | around 67° C.-68° C. |
| Volume flow $v_3$: | around 7.0 l/bottle around 4.2 Nm³/h |

The treatment times of the activating phases are in total less than 10 seconds, it being possible for the treatment times x and y to be different but also to be identical. In addition, it is possible to provide a treatment interval of around four to five seconds between the application phase and the activating phase, i.e. the first method step of the activating phase is then introduced, for example, after a time delay of around five seconds after the introduction of the hydrogen peroxide sterilization medium or after the conclusion of the application phase.

The present application has been described above by way of one possible embodiment. It is obvious that numerous changes and conversions are possible without departing from the teaching concept underlying the present application. Thus it has been assumed above that the treatment heads 6 are part of a treatment machine or device of the rotating type. Obviously the method according to the present application can also be carried out on systems that are realized in the form of linear machines. In addition, it has been assumed above that the introduction of the hydrogen peroxide sterilization medium and the introduction of the activating medium are each effected by means of one and the same treatment head 6. Obviously it is also possible to use different treatment heads in these method steps.

Disclosed is a method for sterilizing bottles, cans, or similar containers by introducing vaporous hydrogen peroxide or a hot hydrogen peroxide sterilization medium into the respective container in an application phase and activating the hydrogen peroxide sterilization medium in an activation phase by introducing a sterile gaseous and/or vaporous hot activation medium, in one possible embodiment hot sterile air, into the respective container.

In at least one embodiment of the present disclosure, rotor 6 is configured to dispose a plurality of activator heads. For example, a single rotor 6 may be configured to treat up to 70,000 bottles per hour, or even more. In at least one embodiment, a controller may be disposed to control the temperature and volume of each pulse of activation medium with respect to a sensed temperature. The controller may be configured to provide starting point data such as initial starting temperatures and volumes of the portions or volumes of the activation medium used to activate the treatment agent. Also, the sensed temperature of the outside of the container may lag behind the actual temperature of the treatment agent inside the container. Therefore, the controller may be configured to control the temperatures and volumes of the pulses of activation medium by taking into account a lag time which may be present. Further, during periods between pulses or when the flow of activating medium is reduced, the treatment agent may continue to react or clean which may increase the temperature of the container being treated. Therefore, the controller may be configured to anticipate a rise in temperature of the treatment agent during a reduction and/or cessation in flow of the activating medium and control the flow of activating medium accordingly. In another embodiment, the rotation of the rotor and movement of ambient air about the containers being cleaned cools the containers. Therefore, the controller may also be configured to take into account cooling of the containers being treated, by ambient air.

In at least one embodiment of the present disclosure, the temperature of the container being treated is kept below a temperature which may distort the container outside of predetermined tolerances. These predetermined tolerances may be shape, dimension, and/or volume tolerances, for example. In at least one embodiment, the predetermined tolerances are maintained to virtually eliminate jamming of the treatment, filling, and closing machines in the filling plant. Predetermined tolerances are also maintained to minimize leaking containers, minimize difficulty in closing containers by assuring screw tops properly fit the treated container, and minimizing variations in the size and shape of the treated containers.

Figure 3:
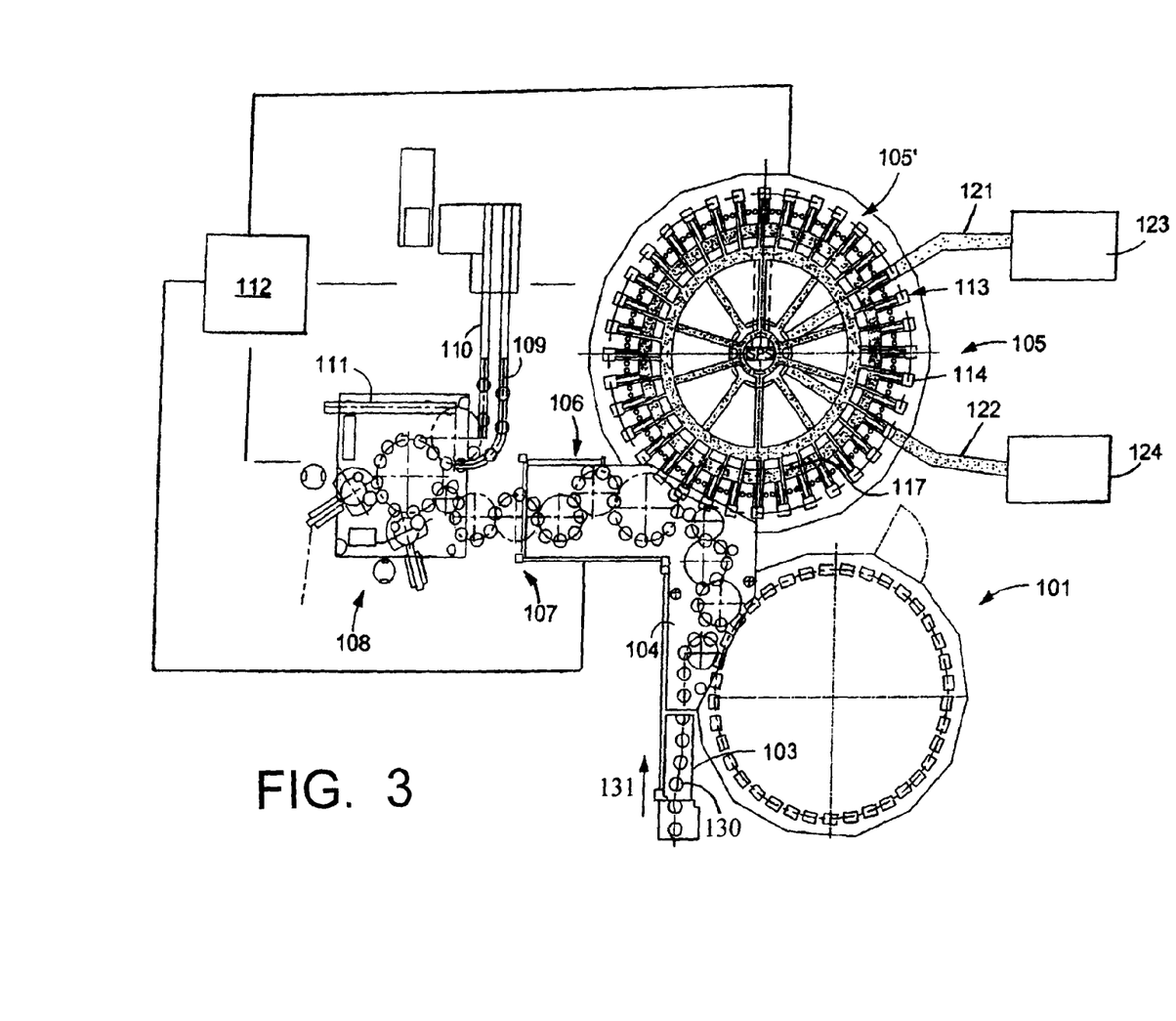
FIG. 3 shows schematically the main components of one possible embodiment example of a system for filling containers, specifically, a beverage bottling plant for filling bottles 130 with at least one liquid beverage, in accordance with at least one possible embodiment.

FIG. 3 shows schematically the main components of one possible embodiment example of a system for filling containers, specifically, a beverage bottling plant for filling bottles 130 with at least one liquid beverage, in accordance with at least one possible embodiment, in which system or plant could possibly be utilized at least one aspect, or several aspects, of the embodiments disclosed herein.

FIG. 3 shows a rinsing arrangement or rinsing station 101, to which the containers, namely bottles 130, are fed in the direction of travel as indicated by the arrow 131, by a first conveyer arrangement 103, which can be a linear conveyor or a combination of a linear conveyor and a starwheel. Downstream of the rinsing arrangement or rinsing station 101, in the direction of travel as indicated by the arrow 131, the rinsed bottles 130 are transported to a beverage filling machine 105 by a second conveyer arrangement 104 that is formed, for example, by one or more starwheels that introduce bottles 130 into the beverage filling machine 105.

The beverage filling machine 105 shown is of a revolving or rotary design, with a rotor 105', which revolves around a central, vertical machine axis. The rotor 105' is designed to receive and hold the bottles 130 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 130 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 3, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle 130, the first product or the second product can be filled by means of an appropriate control of the filling product or fluid valves.

Downstream of the beverage filling machine 105, in the direction of travel of the bottles 130, there can be a beverage bottle closing arrangement or closing station 106 which closes or caps the bottles 130. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 130. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles 130 to different locations.

The first output conveyer arrangement 109, in the embodiment shown, is designed to convey bottles 130 that are filled with a first type of liquid beverage supplied by, for example, the supply reservoir 123. The second output conveyer arrangement 110, in the embodiment shown, is designed to convey bottles 130 that are filled with a second type of liquid beverage supplied by, for example, the supply reservoir 124. The third output conveyer arrangement 111, in the embodiment shown, is designed to convey incorrectly labeled bottles 130. To further explain, the labeling arrangement 108 can comprise at least one beverage bottle inspection or monitoring device that inspects or monitors the location of labels on the bottles 130 to determine if the labels have been correctly placed or aligned on the bottles 130. The third output conveyer arrangement 111 removes any bottles 130 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

One feature or aspect of an embodiment is believed at the time of the filing of this patent application to possibly reside broadly in a method for sterilizing bottles, cans or similar containers 3 by introducing vaporous hydrogen peroxide or a hot hydrogen peroxide sterilization medium into the respective container 3 in an application phase and by activating the hydrogen peroxide sterilization medium in an activating phase by introducing a sterile gaseous and/or vaporous hot activating medium, in one possible embodiment by introducing hot sterile air into the respective container 3, wherein at least during a part phase of the activating phase, the volume flow $v_2$, $v_3$ of the activating medium introduced into the respective container 3 is controlled in dependence on the container temperature $T_{BW}$ or on the temperature of the wall of the container 3.

Another feature or aspect of an embodiment is believed at the time of the filing of this patent application to possibly reside broadly in the method, wherein the volume flow $v_2$, $v_3$ is controlled such that the container temperature $T_{BW}$ corresponds to a required and/or desired temperature $T_{BWrequired}$.

Yet another feature or aspect of an embodiment is believed at the time of the filing of this patent application to possibly reside broadly in the method, wherein the container temperature $T_{BW}$ is measured in a contactless manner.

Still another feature or aspect of an embodiment is believed at the time of the filing of this patent application to possibly reside broadly in the method, wherein the container temperature $T_{BW}$ is measured using a pyrometer.

A further feature or aspect of an embodiment is believed at the time of the filing of this patent application to possibly reside broadly in the method, wherein the activating phase has at least two activating steps, and in that in the last activating step in time, the volume flow $v_3$ of the activating medium supplied to the respective container 3 is controlled in dependence on the container temperature $T_{BW}$.

Another feature or aspect of an embodiment is believed at the time of the filing of this patent application to possibly reside broadly in the method, wherein the volume flow $v_3$ of the second activating phase is forty percent to sixty percent of the volume flow $v_2$ of the first activating phase and is in one possible embodiment fifty percent.

Yet another feature or aspect of an embodiment is believed at the time of the filing of this patent application to possibly reside broadly in the method, wherein in the first method step in time, the volume flow $v_2$ of the activating medium supplied to the respective container 3 is controlled in dependence on the container temperature $T_{BW}$.

Still another feature or aspect of an embodiment is believed at the time of the filing of this patent application to possibly reside broadly in the method, wherein the activating phase has at least two method steps, and in that in the first method step in time at a constant temperature $T_2$ or at a substantially constant temperature and with a constant or substantially constant volume flow $v_2$, the activating medium is supplied into the respective container 3 in a time-controlled manner.

A further feature or aspect of an embodiment is believed at the time of the filing of this patent application to possibly reside broadly in the method, wherein the hot sterilization medium is supplied in a time-controlled manner to the respective container 3 in the application phase at a constant or substantially constant temperature $T_1$.

Another feature or aspect of an embodiment is believed at the time of the filing of this patent application to possibly reside broadly in the method, wherein during the application phase, the hot sterilization medium is supplied to the respective container 3 at a constant or substantially constant temperature and for a constant or substantially constant duration with a volume flow $v_1$ that is stepped or controlled with regard to the container temperature $T_{BW}$ in such a manner that the container temperature $T_{BW}$ remains clearly below the temperature $T_1$ of the hot hydrogen peroxide sterilization medium.

Yet another feature or aspect of an embodiment is believed at the time of the filing of this patent application to possibly reside broadly in the method, wherein during the application phase, the hot hydrogen peroxide sterilization medium is supplied for an application duration of two and a half seconds to four seconds.

Still another feature or aspect of an embodiment is believed at the time of the filing of this patent application to possibly reside broadly in the method, wherein the treatment duration of an activating step is less than ten seconds.

A further feature or aspect of an embodiment is believed at the time of the filing of this patent application to possibly reside broadly in the method, wherein the activating phase is carried out on one single activator.

One feature or aspect of an embodiment is believed at the time of the filing of this patent application to possibly reside broadly in a sterilizing device for containers, such as bottles, beakers, cans and the like for accomplishing the method according to the present application, wherein said sterilization device has at least one device for measuring the temperature of solid body surfaces in a contactless manner and, connected thereto, a computer-controlled control and regulating device for evaluating the measured values and for regulating the temperature and/or volume flow.

Another feature or aspect of an embodiment is believed at the time of the filing of this patent application to possibly reside broadly in the sterilizing device, wherein devices for measuring the temperature of solid body surfaces in a contactless manner are positioned on or in the vicinity of at least a part number of activator heads 9, wherein, in one possible embodiment, a device for measuring the temperature of solid body surfaces in a contactless manner is positioned on or in the vicinity of every activator head 9. Yet another feature or aspect of an embodiment is believed at the time of the filing of this patent application to possibly reside broadly in the sterilizing device, wherein the at least one device for measuring the temperature of solid body surfaces in a contactless manner is a pyrometer.

Still another feature or aspect of an embodiment is believed at the time of the filing of this patent application to possibly reside broadly in the sterilizing device, wherein at least one throttle, one valve or the like is provided to control the volume flow of the activating media.

A further feature or aspect of an embodiment is believed at the time of the filing of this patent application to possibly reside broadly in the sterilizing device, wherein at least one throttle, one valve or the like is positioned in each line path of an activating medium to the respective activator head 9.

Another feature or aspect of an embodiment is believed at the time of the filing of this patent application to possibly reside broadly in a method for the sterilization of bottles, cans or similar containers 3 by introducing a hot hydrogen peroxide sterilization medium into the containers 3 in an application phase and by activation of the hydrogen peroxide sterilization medium in an activation phase by introducing a sterile gaseous and/or vaporous hot activation medium, in one possible embodiment by introducing hot sterile air into the respective container 3, wherein the activation phase has at least two activation steps and in at least the first activation step in time the volume flow $v_2$, $v_3$ of the activation medium introduced into the respective container 3 is regulated as a function of the container temperature $T_{BW}$ or the temperature of the wall of the container 3 or the supplying of the activation medium into the respective container 3 occurs under time control at constant or substantially constant temperature $T_2$ and constant or substantially constant volume flow $v_2$.

Yet another feature or aspect of an embodiment is believed at the time of the filing of this patent application to possibly reside broadly in the method, wherein the volume flow $v_2$, $v_3$ is regulated such that the container temperature $T_{BW}$ corresponds to a nominal temperature $T_{BWsoll}$.

Still another feature or aspect of an embodiment is believed at the time of the filing of this patent application to possibly reside broadly in the method, wherein the container temperature $T_{BW}$ is measured in a noncontact manner.

A further feature or aspect of an embodiment is believed at the time of the filing of this patent application to possibly reside broadly in the method, wherein the container temperature $T_{BW}$ is measured with a pyrometer.

Another feature or aspect of an embodiment is believed at the time of the filing of this patent application to possibly reside broadly in the method, wherein, in the last activation step in time, the volume flow $v_3$ of the activation medium supplied to the respective container 3 is regulated as a function of the container temperature $T_{BW}$.

Yet another feature or aspect of an embodiment is believed at the time of the filing of this patent application to possibly reside broadly in the method, wherein the volume flow $v_3$ of the second activation step amounts to forty percent to sixty percent of the volume flow $v_2$ of the first activation step and in one possible embodiment fifty percent.

Still another feature or aspect of an embodiment is believed at the time of the filing of this patent application to possibly reside broadly in the method, wherein the hot sterilization medium is supplied at constant or substantially constant temperature $T_1$ controlled in time to the respective container 3 in the application phase.

A further feature or aspect of an embodiment is believed at the time of the filing of this patent application to possibly reside broadly in the method, wherein, during the application phase, the hot sterilization medium is supplied to the respective container 3 at constant or substantially constant temperature and over a constant or substantially constant time period with a volume flow $v_1$ that is graduated or controlled in consideration of the container temperature $T_{BW}$ so that the container temperature $T_{BW}$ remains distinctly below the temperature $T_1$ of the hot hydrogen peroxide sterilization medium.

Another feature or aspect of an embodiment is believed at the time of the filing of this patent application to possibly reside broadly in the method, wherein the supplying of the hot hydrogen peroxide sterilization medium during the application phase occurs with an application duration of two and a half seconds to four seconds.

Yet another feature or aspect of an embodiment is believed at the time of the filing of this patent application to possibly reside broadly in the method, wherein the treatment duration of an activation step is less than ten seconds.

Still another feature or aspect of an embodiment is believed at the time of the filing of this patent application to possibly reside broadly in the method, wherein the activation phase is carried out at a single activator.

A further feature or aspect of an embodiment is believed at the time of the filing of this patent application to possibly reside broadly in a sterilization device for containers 3 such as bottles, cups, cans and the like, to carry out the method according to the present application, with at least one activator head for introducing the hot activation medium into the containers 3, wherein this has at least one device for noncontact temperature measurement of surfaces of solid bodies and an interconnected computer-supported control and regulation mechanism, and this for evaluation of measured values and for regulation of the volume flow of the activation medium supplied to the respective container 3, such that in at least the first activation step in time the volume flow $v_2$, $v_3$ of the activation medium introduced into the respective container 3 is regulated as a function of the container temperature $T_{BW}$ or the temperature of the wall of the container 3 or the supplying of the activation medium into the respective container 3 occurs under time control at constant or substantially constant temperature $T_2$ and constant or substantially constant volume flow $v_2$.

One feature or aspect of an embodiment is believed at the time of the filing of this patent application to possibly reside broadly in the sterilization device, wherein, on or in the vicinity of at least some of the activator heads 9, devices are arranged for the noncontact temperature measurement of surfaces of solid bodies, and in one possible embodiment one device for the noncontact temperature measurement of surfaces of solid bodies is arranged on or in the vicinity of each activator head 9.

Another feature or aspect of an embodiment is believed at the time of the filing of this patent application to possibly reside broadly in the sterilization device, wherein the at least one device for the noncontact temperature measurement of surfaces of solid bodies is a pyrometer.

Yet another feature or aspect of an embodiment is believed at the time of the filing of this patent application to possibly reside broadly in the sterilization device, wherein at least one throttle, valve or the like is provided to regulate the volume flow of the activation media.

Still another feature or aspect of an embodiment is believed at the time of the filing of this patent application to possibly reside broadly in the sterilization device, wherein at least one throttle, valve or the like is arranged in each conduit of an activation medium to the respective activator head 9.

A further feature or aspect of an embodiment is believed at the time of the filing of this patent application to possibly reside broadly in a method for the sterilization of bottles, cans or similar containers 3 by introducing a hot hydrogen peroxide sterilization medium into the containers 3 in an application phase and by activation of the hydrogen peroxide sterilization medium in an activation phase by introducing a sterile gaseous and/or vaporous hot activation medium, in one possible embodiment by introducing hot sterile air into the respective container 3, wherein the activation phase has at least two activation steps, that in at least the first activation step in time the volume flow $v_2$, $v_3$ of the activation medium introduced into the respective container 3 is regulated as a function of the container temperature $T_{BW}$ or the temperature of the wall of the container 3 or the supplying of the activation medium into the respective container 3 occurs under time control at constant or substantially constant temperature $T_2$ and constant or substantially constant volume flow $v_2$, and that in the second activation step to regulate the container temperature $T_{BW}$ the volume flow $v_3$ of the activation medium introduced into the container 3 amounts to forty percent to sixty percent of the volume flow $v_2$ of the first activation step.

Another feature or aspect of an embodiment is believed at the time of the filing of this patent application to possibly reside broadly in the method, wherein the volume flow $v_2$, $v_3$ is regulated such that the container temperature $T_{BW}$ corresponds to a nominal temperature $T_{BWsoll}$.

Yet another feature or aspect of an embodiment is believed at the time of the filing of this patent application to possibly reside broadly in the method, wherein the container temperature $T_{BW}$ is measured in a noncontact manner.

Still another feature or aspect of an embodiment is believed at the time of the filing of this patent application to possibly reside broadly in the method, wherein the container temperature $T_{BW}$ is measured with a pyrometer.

A further feature or aspect of an embodiment is believed at the time of the filing of this patent application to possibly reside broadly in the method, wherein, in the last activation step in time, the volume flow $v_3$ of the activation medium supplied to the respective container 3 is regulated as a function of the container temperature $T_{BW}$.

Another feature or aspect of an embodiment is believed at the time of the filing of this patent application to possibly reside broadly in the method, wherein the volume flow $v_3$ of the activation medium introduced into the container 3 in the second activation step amounts to fifty percent of the volume flow $v_2$ of the first activation step.

Yet another feature or aspect of an embodiment is believed at the time of the filing of this patent application to possibly reside broadly in the method, wherein the hot sterilization medium is supplied at constant or substantially constant temperature $T_1$ controlled in time to the respective container 3 in the application phase.

Still another feature or aspect of an embodiment is believed at the time of the filing of this patent application to possibly reside broadly in the method, wherein, during the application phase, the hot sterilization medium is supplied to the respective container 3 at constant or substantially constant temperature and over a constant or substantially constant time period with a volume flow $v_1$ that is graduated or controlled in consideration of the container temperature $T_{BW}$ so that the container temperature $T_{BW}$ remains distinctly below the temperature $T_1$ of the hot hydrogen peroxide sterilization medium.

A further feature or aspect of an embodiment is believed at the time of the filing of this patent application to possibly reside broadly in the method, wherein the supplying of the hot hydrogen peroxide sterilization medium during the application phase occurs with an application duration of two and a half seconds to four seconds.

One feature or aspect of an embodiment is believed at the time of the filing of this patent application to possibly reside broadly in the method, wherein the treatment duration of an activation step is less than ten seconds.

Another feature or aspect of an embodiment is believed at the time of the filing of this patent application to possibly reside broadly in the method, wherein the activation phase is carried out at a single activator.

Yet another feature or aspect of an embodiment is believed at the time of the filing of this patent application to possibly reside broadly in a sterilization device for containers 3 such as bottles, cups, cans and the like, to carry out the method according to the present application, with at least one activator head for introducing the hot activation medium into the containers 3, wherein this has at least one device for noncontact temperature measurement of surfaces of solid bodies and an interconnected computer-supported control and regulation mechanism, and this for evaluation of measured values and for regulation of the volume flow of the activation medium supplied to the respective container 3, such that, having at least two activation steps, in at least the first activation step in time the volume flow $v_2$, $v_3$ of the activation medium introduced into the respective container 3 is regulated as a function of the container temperature $T_{BW}$ or the temperature of the wall of the container 3 or the supplying of the activation medium into the respective container 3 occurs under time control at constant or substantially constant temperature $T_2$ and constant or substantially constant volume flow $v_2$, and furthermore in the second activation step to regulate the container temperature $T_{BW}$ the volume flow $v_3$ of the activation medium introduced into the container 3 amounts to forty percent to sixty percent of the volume flow $v_2$ of the first activation step.

Still another feature or aspect of an embodiment is believed at the time of the filing of this patent application to possibly reside broadly in the sterilization device, wherein, on or in the vicinity of at least some of the activator heads 9, devices are arranged for the noncontact temperature measurement of surfaces of solid bodies, and in one possible embodiment one device for the noncontact temperature measurement of surfaces of solid bodies is arranged on or in the vicinity of each activator head 9.

A further feature or aspect of an embodiment is believed at the time of the filing of this patent application to possibly reside broadly in the sterilization device, wherein the at least one device for the noncontact temperature measurement of surfaces of solid bodies is a pyrometer.

Another feature or aspect of an embodiment is believed at the time of the filing of this patent application to possibly reside broadly in the sterilization device, wherein at least one throttle, valve or the like is provided to regulate the volume flow of the activation media.

Yet another feature or aspect of an embodiment is believed at the time of the filing of this patent application to possibly reside broadly in the sterilization device, wherein at least one throttle, valve or the like is arranged in each conduit of an activation medium to the respective activator head 9.

One feature or aspect of an embodiment is believed at the time of the filing of this patent application to possibly reside broadly in a method of operating a container filling plant for filling plastic containers with a filling material, the method comprising steps to minimize distortion of plastic containers to be filled and maximize throughput of plastic containers by controlling the temperature of a container to be filled, said container filling plant comprising: a controller arrangement disposed and configured to monitor and control said container filling plant and to regulate control valves controlling a flow of activation medium; a filling machine being configured and disposed to fill empty plastic containers with a filling material; a first moving arrangement being configured and disposed to move plastic containers to said filling machine; a closing machine being configured and disposed to close filled plastic containers; a second moving arrangement being configured and disposed to accept filled plastic containers from said filling machine and to move filled plastic containers out of said filling machine and to said closing machine; a rotary treatment machine being configured and disposed to treat plastic containers prior to filling; a third moving arrangement being configured and disposed to move plastic containers to said treatment machine; said first moving arrangement being configured and disposed to move treated plastic containers from said treatment machine to said filling machine; said treatment machine comprising: at least one treatment device being configured and disposed to treat plastic containers upon the plastic containers being within said treatment machine; and said at least one treatment device comprising: a source of a treatment agent, which treatment agent is configured to be heated to treat the inside surface of a plastic container to be treated; a heater being configured and disposed to heat the treatment agent to a predetermined temperature, above a temperature of a container to be treated; a dispensing arrangement being configured to dispense heated treatment agent into a plastic container, which heated treatment agent is in sufficient amount and at a sufficient temperature to sufficiently coat the inside surface of the plastic container with condensed treatment agent to treat the plastic container, upon contact of the heated treatment agent on the inside surface of the container being treated; said dispensing arrangement also being configured to dispense a first and a second volume of heated activation medium into the plastic container, which heated activation medium is at a temperature sufficient to activate the condensed treatment agent; a non-contact temperature measuring apparatus configured and disposed to measure a temperature, on or within the outer surface, of the plastic container being treated and to send the sensed temperature to the controller arrangement said method comprising the steps of: moving a plastic container into said treatment machine to be treated; heating the treatment agent to a temperature greater than a temperature of the plastic container to be treated; dispensing treatment agent into the plastic container being treated in an amount sufficient to coat the inside surface of the plastic container with a sufficient amount of condensate of the treatment agent to treat the plastic container; condensing at least a portion of the treatment agent on the inside surface of the plastic container being treated and coating the inside surface of the plastic container being treated with a sufficient amount of condensate to sufficiently clean the container to increase the shelf life of contents of the filled container to a substantially predetermined shelf life; dispensing a first volume of heated activation medium into the plastic container being treated in an amount sufficient to heat the treatment agent to a temperature sufficient to treat the plastic container and heating the container to be filled to a first, predetermined, temperature; sensing a temperature on or within the outer surface of the plastic container being treated with the non-contact temperature measuring apparatus; sending the sensed temperature to the controller arrangement; controlling the first volume of heated activation medium being dispensed into the plastic container being treated, with the control valves, to an amount sufficient to heat the treatment agent to a temperature sufficient to treat the plastic container and heating the container to be filled to the first, predetermined, temperature, the first, predetermined, temperature being a temperature just below the temperature at which the plastic container will distort outside of predetermined tolerances; reducing the flow of heated activation medium into the plastic container being treated, upon or just before the container to be filled reaching the first, predetermined, temperature, by an amount sufficient to permit cooling, during rotation of the plastic container in the treatment machine, the treatment agent and plastic container cooling to a second, lower, temperature; dispensing a second volume of heated activation medium into the already heated plastic container being treated and increasing the temperature of the treatment agent to a temperature sufficient to treat the plastic container and increasing the temperature of the container to be filled to the first, predetermined, temperature, the second volume of heated activation medium being smaller than the first volume of activation medium and at essentially the same temperature as the first volume of activation medium, the second volume being sufficient to activate the treatment agent to finally clean the container being treated and increase the shelf life of contents of the filled container to a substantially predetermined shelf life and to not distort the plastic container outside of predetermined tolerances; moving the treated plastic container from said dispensing arrangement to said filling machine; filling the treated plastic container; moving the treated, filled plastic container to said closing machine; closing the treated, filled plastic container.

Another feature or aspect of an embodiment is believed at the time of the filing of this patent application to possibly reside broadly in a method of operating a container filling plant for filling plastic containers with a filling material further comprising one of a), b), c), d), and e): a) controlling the temperature of the heated treatment agent at a substantially constant temperature; b) controlling the temperature of the heated treatment agent at a substantially constant temperature; and controlling the volume of the heated treatment agent to keep a temperature of the plastic container being sterilized below the temperature at which the plastic container will distort outside of predetermined tolerances; c) controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; d) controlling the temperature of the heated treatment agent at a substantially constant temperature; controlling the volume of the heated treatment agent to keep a temperature of the plastic container being sterilized below the temperature at which the plastic container will distort outside of predetermined tolerances; controlling the time period of said step of dispensing a heated treatment agent into a plastic container being sterilized between a range of about 2.5 seconds to about 4 seconds; and all said steps of treating a single plastic container are carried out in less than about 10 seconds; and e) controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; all said steps of treating single plastic container are carried out in less than about 10 seconds; and said step of disposing said first volume of heated activation medium into the plastic container being treated and step of disposing said second volume of heated activation medium into the plastic container being treated are carried out with a single activator.

Yet another feature or aspect of an embodiment is believed at the time of the filing of this patent application to possibly reside broadly in a method of sterilizing plastic containers of wherein said non-contact temperature measuring apparatus is a pyrometer.

Still another feature or aspect of an embodiment is believed at the time of the filing of this patent application to possibly reside broadly in a method of sterilizing plastic containers wherein said step of dispensing said second volume of heated activation medium further comprises one of a), b), and c): a) controlling said second volume of heated activation medium to have a volume within a range of about 40% to about 60% of the volume of said first volume of heated activation medium dispensed into the plastic container being treated; b) controlling said second volume of heated activation medium to have a volume of about 50% of the volume of said first volume of heated activation medium dispensed into the plastic container being treated; and c) controlling said second volume of heated activation medium dispensed into the plastic container being treated as a function of said sensed temperature on or within the outer surface of the plastic container.

A further feature or aspect of an embodiment is believed at the time of the filing of this patent application to possibly reside broadly in a method of sterilizing plastic containers comprising the steps of: dispensing a heated treatment agent comprising hydrogen peroxide into a plastic container being sterilized in an amount and temperature sufficient to condense and coat the inside surface of the plastic container, with a sufficient amount of condensate to sterilize the plastic container; condensing at least a portion of said heated treatment agent on the inside surface of the plastic container being sterilized and coating the inside surface of the plastic container being sterilized with a sufficient amount of condensate to sufficiently clean the container; dispensing a first volume of heated sterile gas into the plastic container being sterilized in an amount sufficient to heat the treatment agent to a temperature sufficient to at least partially sterilize the plastic container and heating the container to be filled to a first, predetermined, temperature; sensing a temperature on or within the outer surface of the plastic container being sterilized with a temperature measuring apparatus; controlling the first volume of heated sterile gas being dispensed into the plastic container being sterilized to an amount sufficient to heat the treatment agent to a temperature sufficient to at least partially sterilize the plastic container and heating the container to be filled to the first, predetermined, temperature, the first, predetermined, temperature being a temperature below the temperature at which the plastic container will distort outside of predetermined tolerances; dispensing a second volume of heated sterile gas into the already heated plastic container being sterilized, the second volume of heated sterile gas being smaller than the first volume of heated sterile gas, the second volume being sufficient to activate the treatment agent to sterilize the container being sterilized and to not distort the container being sterilized outside of predetermined tolerances.

Another feature or aspect of an embodiment is believed at the time of the filing of this patent application to possibly reside broadly in a method of sterilizing plastic containers further comprising the step of reducing said flow of said first determined portion of heated sterilized air in the container being sterilized, after said step of dispensing said first determined portion of heated sterilized air.

Yet another feature or aspect of an embodiment is believed at the time of the filing of this patent application to possibly reside broadly in a method of sterilizing plastic containers wherein said step of sensing said temperature on or within the outer surface of the plastic container being sterilized comprises sensing said temperature without contacting the plastic container being sterilized.

Still another feature or aspect of an embodiment is believed at the time of the filing of this patent application to possibly reside broadly in a method of sterilizing plastic containers further comprising one of a), b), c), d), e), and f): a) said step of sensing said temperature on or within the outer surface of the plastic container being sterilized comprises sensing said temperature with a pyrometer; b) said step of sensing said temperature on or within the outer surface of the plastic container being sterilized comprises sensing said temperature with a pyrometer; and controlling the temperature of the heated treatment agent at a substantially constant temperature; c) said step of sensing said temperature on or within the outer surface of the plastic container being sterilized comprises sensing said temperature with a pyrometer; controlling the temperature of the heated treatment agent at a substantially constant temperature; and controlling the volume of the heated treatment agent to keep a temperature of the plastic container being sterilized below the temperature at which the plastic container will distort outside of predetermined tolerances; d) said step of sensing said temperature on or within the outer surface of the plastic container being sterilized comprises sensing said temperature with a pyrometer; controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; e) said step of sensing said temperature on or within the outer surface of the plastic container being sterilized comprises sensing said temperature with a pyrometer; controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; and all said steps of sterilizing a single plastic container are carried out in less than about 10 seconds; and f) said step of sensing said temperature on or within the outer surface of the plastic container being sterilized comprises sensing said temperature with a pyrometer; controlling the temperature of the heated treatment agent at a substantially constant temperature; controlling the volume of the heated treatment agent to keep a temperature of the plastic container being sterilized below the temperature at which the plastic container will distort outside of predetermined tolerances; and controlling the time period of said step of dispensing a heated treatment agent into a plastic container being sterilized between a range of about 2.5 seconds to about 4 seconds; all said steps of sterilizing single plastic container are carried out in less than about 10 seconds; and said step of disposing said first volume of heated activation medium into the plastic container being sterilized and step of disposing said second volume of heated activation medium into the plastic container being sterilized are carried out with a single activator.

A further feature or aspect of an embodiment is believed at the time of the filing of this patent application to possibly reside broadly in a method of sterilizing plastic containers wherein said step of dispensing said second volume of heated activation medium further comprises one of a), b), and c): a) controlling said second volume of heated activation medium to have a volume within a range of about 40% to about 60% of the volume of said first volume of heated activation medium dispensed into the plastic container being treated; b) controlling said second volume of heated activation medium to have a volume of about 50% of the volume of said first volume of heated activation medium dispensed into the plastic container being treated; and c) controlling said second volume of heated activation medium dispensed into the plastic container being treated as a function of said sensed temperature on or within the outer surface of the plastic container.

Another feature or aspect of an embodiment is believed at the time of the filing of this patent application to possibly reside broadly in a method of treating plastic containers comprising the steps of: heating a treatment agent to a temperature greater than a temperature of a plastic container to be treated; dispensing said heated treatment agent into the plastic container being treated in an amount sufficient to coat the inside surface of the plastic container with a sufficient amount of condensate of the treatment agent to treat the plastic container; condensing at least a portion of said heated treatment agent on the inside surface of the plastic container being treated and coating the inside surface of the plastic container being treated with a sufficient amount of condensate to sufficiently clean the plastic container; dispensing a first volume of heated activation medium into the plastic container being treated in an amount sufficient to heat the treatment agent to a temperature sufficient to treat the plastic container and heating the container to be filled to a first, predetermined, temperature; sensing a temperature on or within the outer surface of the plastic container being treated with a temperature measuring apparatus; controlling the first volume of heated activation medium being dispensed into the plastic container being treated to an amount sufficient to heat the treatment agent to a temperature sufficient to treat the plastic container and heating the container to be filled to the first, predetermined, temperature, the first, predetermined, temperature being a temperature below the temperature at which the plastic container will distort outside of predetermined tolerances; dispensing a second volume of heated activation medium into the already heated plastic container being treated, the second volume of heated activation medium being smaller than the first volume of activation medium, the second volume being sufficient to activate the treatment agent to clean the container being treated and keep the container being treated below the temperature at which the plastic container will distort outside of predetermined tolerances.

Yet another feature or aspect of an embodiment is believed at the time of the filing of this patent application to possibly reside broadly in a method of treating plastic containers wherein said step of dispensing said second volume of heated activation medium further comprises one of a), b), and c): a) controlling said second volume of heated activation medium to have a volume within a range of about 40% to about 60% of the volume of said first volume of heated activation medium dispensed into the plastic container being treated; b) controlling said second volume of heated activation medium to have a volume of about 50% of the volume of said first volume of heated activation medium dispensed into the plastic container being treated; and c) controlling said second volume of heated activation medium dispensed into the plastic container being treated as a function of said sensed temperature on or within the outer surface of the plastic container.

One feature or aspect of an embodiment is believed at the time of the filing of this patent application to possibly reside broadly in a method of treating containers of wherein said step of sensing said temperature on or within the outer surface of the container being treated comprises sensing said temperature without contacting the container being treated.

Another feature or aspect of an embodiment is believed at the time of the filing of this patent application to possibly reside broadly in a method of treating containers of wherein said step of sensing said temperature on or within the outer surface of the container being treated comprises sensing said temperature of the container being treated with a pyrometer.

Yet another feature or aspect of an embodiment is believed at the time of the filing of this patent application to possibly reside broadly in a method of treating containers wherein said step of dispensing a heated treatment agent into a container being treated further comprises controlling the temperature of the heated treatment agent at a substantially constant temperature.

Still another feature or aspect of an embodiment is believed at the time of the filing of this patent application to possibly reside broadly in a method of treating containers wherein said step of dispensing a heated treatment agent into a container being treated further comprises controlling the volume of the heated treatment agent to keep a temperature of the container being treated below the temperature at which the container will distort outside of predetermined tolerances.

A further feature or aspect of an embodiment is believed at the time of the filing of this patent application to possibly reside broadly in a method of treating containers wherein said step of dispensing a heated treatment agent into a container being treated further comprises controlling the time period of said step of dispensing a heated treatment agent into a container being treated between a range of about 2.5 seconds to about 4 seconds.

Another feature or aspect of an embodiment is believed at the time of the filing of this patent application to possibly reside broadly in a method of treating containers wherein all said steps of treating a single container are carried out in less than about 10 seconds.

Yet another feature or aspect of an embodiment is believed at the time of the filing of this patent application to possibly reside broadly in a method of treating containers wherein said step of disposing said first volume of heated activation medium into the container being treated and step of disposing said second volume of heated activation medium into the container being treated are carried out with a single activator.

Still another feature or aspect of an embodiment is believed at the time of the filing of this patent application to possibly reside broadly in a method of treating plastic containers further comprising the step of reducing said flow of said first volume of heated activation medium in the container being treated, after said step of dispensing said first volume of heated activation medium.

A further feature or aspect of an embodiment is believed at the time of the filing of this patent application to possibly reside broadly in a method of treating plastic containers wherein said heated treatment agent comprised hydrogen peroxide and said first and said second volumes of heated activation medium comprise sterile air.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . ." may possibly not be used or useable in any one or more embodiments of the application.

The sentence immediately above relates to patents, published patent applications and other documents either incorporated by reference or not incorporated by reference.

All of the patents, patent applications or patent publications, which were cited in the German Office Action dated Dec. 10, 2007, and/or cited elsewhere are hereby incorporated by reference as if set forth in their entirety herein as follows: DE 10 2004 030 956, having the following English translation of the German title "Sterilization of containers, especially plastics bottles for drinks, by blowing in hydrogen peroxide vapor and hot air then blowing in air at sufficiently high flow rate to avoid excessive container temperature,"

published on Jan. 12, 2006; EP 0 590 505, having the following English translation of the German title "Apparatus and control for heat treatment and sterilizing of bottles or containers," published on Apr. 6, 1994; DE 10 2005 018 382, having the following English translation of the German title "Bottle washing machine, for cleaning bottles carried through on conveyor, measures final bottle temperatures to determine that hot detergent has been fully rinsed clear by cold water," published on Oct. 26, 2006; DE 198 46 322, having the following English translation of the German title 1345 "Monitoring treatment of internal vol. of bottles or vessels by rinser involves detecting flow of fluid introduced into interior of bottle, as it emanates from open mouth of bottle," published on Apr. 13, 2000; DE 199 49 692, having the following English translation of the German title "Sterilization of temperature-sensitive especially polyethylene terephthalate bottles moving on a conveyor, using a peroxide aerosol and sterile air," published on Apr. 19, 2001; and WO 2006/053745, having the following English translation of the German title "PROCESS AND DEVICE FOR STERILISING CONTINUOUSLY CONVEYED PLASTIC BOTTLES," published on May 26, 2006.

All of the patents, patent applications or patent publications, which were cited in the International Search Report dated Jun. 30, 2008, and/or cited elsewhere are hereby incorporated by reference as if set forth in their entirety herein as follows: U.S. Pat. No. 6,702,985, having the title "Apparatus and method for providing container interior sterilization in an aseptic processing apparatus," published on Mar. 9, 2004; and WO 2007/134803, having the following English translation of the German title "METHOD AND DEVICE FOR STERILIZING BOTTLES OR SIMILAR CONTAINERS," published on Nov. 29, 2007.

Also, hereby incorporated by reference as if set forth in their entirety herein are U.S. patent application Ser. No. 12/605,550 and WIPO patent publication no. WO/2008/135165. U.S. Patent Application No. 12/605,550 is a Continuation-In-Part application of WO/2008/135165, having International Patent Application No. PCT/EP2008/003247, filed on Apr. 23, 2008, which claims priority from Federal Republic of Germany Patent Application No. 10 2007 020 457.6, filed on Apr. 27, 2007.

Some examples of non-contact temperature measuring devices or pyrometers that may possibly be utilized or adapted for use in at least one possible embodiment may possibly be found in the following: those temperature measuring devices manufactured and sold by Clark Pyrometers, 10 Brent Dr., Hudson Mass.; those manufactured and sold by Radiant Innovation, HsinChu, Taiwan; those manufactured and sold by Omega Engineering Inc., 1 Omega Drive, Stamford, Conn. Still other devices which may possibly be used in at least one possible embodiment of the present application may possibly include the optical pyrometer types disclosed in: Hartel U.S. Pat. No. 5,398,734 (KHS Machinen-und Anlagenban Aktiengesellschaft); Green U.S. Pat. No. 3,535, 522 (Glass Container Industry Research) and Howell U.S. Pat. Nos. 2,987,589 and 2,869,369 (Servo Corp. of America), the disclosures of which are all hereby incorporated by reference as if set forth in their entirety herein. Some examples of infrared thermometers which may possibly be used in at least one possible embodiment of the present application may possibly be found in the following US patents: Heinke et al. U.S. Pat. No. 5,81,410, and Christol et al. U.S. Pat. No. 4,634,294 (both assigned to Raytek, Inc.), the disclosures of which are also all hereby incorporated by reference as if set forth in their entirety herein.

An example of a device configured to inject hydrogen peroxide into a container for sterilization, which may possibly be utilized or adapted for use in at least one possible embodiment of the present application, may possibly be found in the following U.S. Pat. No. 7,010,900, having the title "Beverage bottling plant for filling bottles with a liquid beverage filling material, and a cleaning device for cleaning bottles in a beverage bottling plant," published on Mar. 14, 2006.

The patents, patent applications, patent publications, and other publications listed herein are incorporated by reference in their entirety herein, except words relating to the opinions and judgments of the author and not directly relating to the technical details of the description of the embodiments therein are not incorporated by reference. The purpose of incorporating U.S. patents, Foreign patents, patent publications, and other publications is solely to provide additional information relating to technical features of one or more embodiments, which information may not be completely disclosed in the wording in the pages of this application. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not to be incorporated by reference herein.

The corresponding foreign and international patent publication applications, namely, Federal Republic of Germany Patent Application No. 10 2007 020 458.4, filed on Apr. 27, 2007, having inventors Daryoush and Thomas HEROLD, and DE-OS 10 2007 020 458.4 and DE-PS 10 2007 020 458.4, and International Application No. PCT/EP2008/002858, filed on Apr. 11, 2008, having WIPO Publication No. WO 2008/135132 and inventors Daryoush and Thomas HEROLD, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the corresponding foreign equivalent patent application(s), that is, PCT/EP2008/002858 and German Patent Application 10 2007 020 458.4, is solely for the purpose of providing a basis of correction of any wording in the pages of the present application, which may have been mistranslated or misinterpreted by the translator. Words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned word in this sentence, when not used to describe technical features of one or more embodiments, are not generally considered to be incorporated by reference herein.

Statements made in the original foreign patent applications PCT/EP2008/002858 and DE 10 2007 020 458.4 from which this patent application claims priority which do not have to do with the correction of the translation in this patent application are not to be included in this patent application in the incorporation by reference.

Any statements about admissions of prior art in the original foreign patent applications PCT/EP2008/002858 and DE 10 2007 020 458.4 are not to be included in this patent application in the incorporation by reference, since the laws relating to prior art in non-U.S. Patent Offices and courts may be substantially different from the Patent Laws of the United States.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A method of sterilizing containers comprising:
    introducing heated or vaporous hydrogen peroxide into a container;
    activating said hydrogen peroxide in said container in an activation phase comprising a first step and a second step subsequent to said first step;
    said first step comprising conducting heated gaseous and/or vaporous activation medium into said container;
    said second step comprising:
        conducting additional activation medium into said container at a second volume flow rate, lower than a first volume flow rate of said activation medium in said first step, while simultaneously monitoring a temperature of at least a portion of said container; and
        adjusting said second volume flow rate, as needed based on the monitored temperature of said at least a portion of said container, throughout said second step; and
    said step of introducing said heated or vaporous hydrogen peroxide comprising heating and supplying said heated or vaporous hydrogen peroxide at a constant or substantially constant temperature over a constant or substantially constant time with a third volume flow that is controlled based on the monitored container temperature so that the container temperature remains substantially below the temperature of said heated or vaporous hydrogen peroxide.

2. The method according to claim 1, wherein said second volume flow rate is 40%-60% of said first volume flow rate, or said second volume flow rate is 50% of said first volume flow rate.

3. The method according to claim 2, wherein said method further comprises setting and maintaining the temperature of said container essentially at a desired temperature by regulating said volume flow rates.

4. The method according to claim 3, wherein said step of monitoring comprises measuring the temperature using a pyrometer.

5. The method according to claim 4, wherein said first step comprises regulating said first volume flow rate based on the monitored temperature of said container.

6. The method according to claim 5, wherein said first step comprises delivering activation medium at a constant or substantially constant temperature and at a constant or substantially constant flow rate for a predetermined time.

7. The method according to claim 6, wherein the heated hydrogen peroxide is supplied for a time of 2.5 to 4 seconds.

8. The method according to claim 7, wherein said first and second volume flows of the activation medium are supplied over a total time less than 10 seconds.

9. The method according to claim 8, wherein said first and second volume flows are supplied by a single activator.

10. The method according to claim 1, wherein said method further comprises setting and maintaining the temperature of said container essentially at a desired temperature by regulating said volume flow rates.

11. The method according to claim 1, wherein said step of monitoring comprises measuring the temperature using a pyrometer.

12. The method according to claim 1, wherein said first step comprises regulating said first volume flow rate based on the monitored temperature of said container.

13. The method according to claim 1, wherein said first step comprises delivering activation medium at a constant or substantially constant temperature and at a constant or substantially constant flow rate for a predetermined time.

14. The method according to claim 1, wherein the heated hydrogen peroxide is supplied for a time of 2.5 to 4 seconds, and said first and second volume flows of the activation medium are supplied over a total time less than 10 seconds.

15. A sterilization arrangement comprising:
a first delivery arrangement to introduce heated hydrogen peroxide into a container;
a second delivery arrangement to:
introduce a heated gaseous and/or vaporous activation medium into the container at a first volume flow rate in a first step; and
subsequently introduce said activation medium into the container at a second, lesser, volume flow rate in a second step;
a monitoring arrangement to monitor, without contact, the temperature of said container or the wall of said container;
a computer control arrangement to regulate said second volume flow rate based on the monitored temperature;
said second delivery arrangement comprising:
activator heads for dispensing activation medium into containers; and
control devices, comprising throttles or valves, configured to control the flow of said activation medium to said activator heads;
a detection arrangement comprising temperature detection devices for contactless measurement of the temperature of the surfaces of solid bodies;
each temperature detection device being positioned on or at each of said activator heads or a plurality of said activator heads; and
said computer control arrangement is configured to control said first delivery arrangement to introduce said heated hydrogen peroxide at a constant or substantially constant temperature over a constant or substantially constant time with a third volume flow that is controlled based on the monitored container temperature so that the container temperature remains substantially below the temperature of the heated hydrogen peroxide.

16. The sterilization arrangement according to claim 15, wherein said at least one temperature detection device comprises a pyrometer.

* * * * *